United States Patent

Waller et al.

[11] Patent Number: 5,969,811
[45] Date of Patent: Oct. 19, 1999

[54] SPECTRAL ANALYZER

[76] Inventors: Michael V. Waller, 834 Tarpon Ave., Fernandina Beach, Fla. 32034; Kenneth Arsenault, 2 Hutchinson Rd., Ware, Mass. 01082

[21] Appl. No.: 09/139,210

[22] Filed: Aug. 24, 1998

[51] Int. Cl.$^6$ ..................................... G01N 1/10
[52] U.S. Cl. .......................... 356/246; 356/440; 250/576
[58] Field of Search ................... 356/246, 244, 356/236, 432, 436, 437, 440, 448, 435; 250/343, 373, 374, 576, 228

[56] References Cited

U.S. PATENT DOCUMENTS

| | | | |
|---|---|---|---|
| 3,591,287 | 7/1971 | Hannis | 356/244 |
| 3,792,272 | 2/1974 | Harte et al. | 356/437 |
| 5,125,742 | 6/1992 | Wilks, Jr. | 356/246 |
| 5,273,633 | 12/1993 | Wang | 356/246 |
| 5,340,986 | 8/1994 | Wong | 356/437 |
| 5,341,214 | 8/1994 | Wong | 356/437 |
| 5,428,222 | 6/1995 | Alexay | 250/343 |
| 5,459,566 | 10/1995 | Pearson et al. | 356/246 |
| 5,815,258 | 9/1998 | Nakanishi | 356/246 |

*Primary Examiner*—Hoa Q. Pham
*Attorney, Agent, or Firm*—Hovey, Williams, Timmons & Collins

[57] ABSTRACT

A compact, lightweight, and inexpensive spectral analyzer (10) that creates a highly concentrated and collimated beam of light and that has a long optical path length that improves the analyzer's signal-to-noise ratio is disclosed. The spectral analyzer includes an optical collector assembly (12), a specimen holder (14), and an optical detector (16). The collector assembly includes a collector housing (18) having a plurality of spaced, internally reflective walls (22,24) and an exit aperture (26) through one of the walls, and a light source (20) positioned between the reflective walls. The light rays emitted from the light source are collected and collimated by the reflective walls into a highly concentrated beam of parallel light rays that is directed out of the exit aperture. The specimen holder is positioned adjacent the exit aperture of the collector for receiving the collimated beam. The collector assembly and specimen holder are positioned relative to one another so that the collimated beam is directed into the specimen holder at a pre-selected fixed angle. The specimen holder is polygonal in cross section and includes a plurality of internally reflective surfaces for reflecting the collimated beam at the pre-selected fixed angle along an optical path that is substantially longer than the specimen holder. The optical detector is positioned in or adjacent to the specimen holder for detecting the collimated beam after it has been reflected by the internally reflective surfaces of the specimen holder.

13 Claims, 1 Drawing Sheet

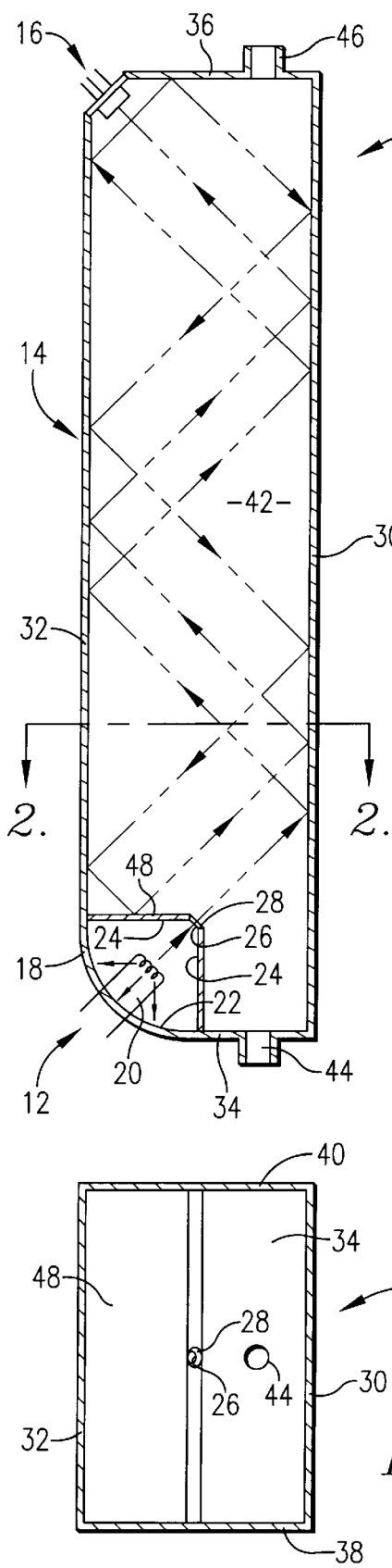
FIG.1.
FIG.2.
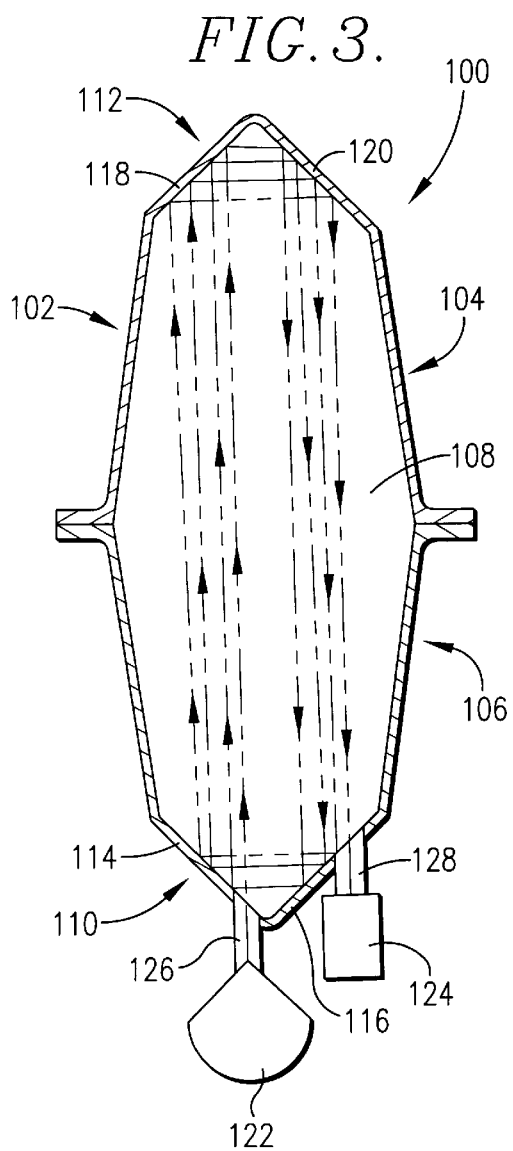
FIG.3.

SPECTRAL ANALYZER

BACKGROUND OF THE INVENTION

1. Field of the Invention

The present invention relates to spectral analyzers. More particularly, the invention relates to a lightweight and compact spectral analyzer that creates a highly concentrated and collimated beam of light and then reflects the beam along a relatively long optical path length for improving the analyzer's signal-to-noise ratio without the use of complicated and expensive optical imaging equipment.

2. Description of the Prior Art

Spectral analyzers are commonly used in the analysis of various types of gas, solid, and liquid specimens. Typical spectral analyzers include a specimen holder for receiving a specimen to be analyzed, a light source for directing light rays through the specimen holder and the specimen contained therein, and an optical detector for detecting the light rays after they have passed through the specimen and for producing representative signals. The detector signals are then analyzed to determine the effect that the specimen had upon the light rays to determine characteristics of the specimen such as the presence and/or concentration of a particular compound in the specimen.

One significant problem associated with prior art spectral analyzers is that they suffer from low signal-to-noise ratios resulting from low detectable light levels and relatively short optical path lengths. One prior art solution to this problem is to focus more light energy through a short optical path length to increase the detectable light levels. This design, however, is limited by Beer-Lambert absorption problems. Other prior art attempts to solve this problem involve the use of complex and expensive imaging optical components coupled with reflective chambers. Although these devices have improved signal-to-noise ratios, they are too complicated and expensive for most applications.

Accordingly, there is a need for a relatively compact, lightweight, and inexpensive spectral analyzer that achieves a relatively high signal-to-noise ratio without the use of complicated and expensive optical equipment.

OBJECTS AND SUMMARY OF THE INVENTION

The present invention solves the above-described problems and provides a distinct advance in the art of spectral analyzers. More particularly, the present invention provides a relatively compact, lightweight, and inexpensive spectral analyzer that achieves a high signal-to-noise ratio with a simple and cost-effective design.

The spectral analyzer of the present invention broadly includes an optical collector assembly, a specimen holder, and an optical detector. The collector assembly includes a collector housing and a light source positioned within the housing. The collector housing includes a plurality of spaced, internally reflective walls with an exit aperture formed through one of the walls. The light source is positioned between the reflective walls so that light rays emitted therefrom reflect from the walls and are collected and collimated into a highly concentrated beam of parallel light rays that is directed out of the exit aperture.

The specimen holder is configured for holding a liquid, gas, or solid sample and is positioned adjacent the exit aperture of the collector assembly for receiving the collimated beam. The collector assembly and specimen holder are positioned relative to one another so that the collimated beam is directed into the specimen holder at a pre-selected fixed angle. The specimen holder is preferably polygonal in cross section and includes a plurality of internally reflective surfaces for repeatedly reflecting the collimated beam at the pre-selected fixed angle along an optical path that is substantially longer than the specimen holder.

The optical detector is positioned in or adjacent to the specimen holder for detecting the collimated beam after it has been reflected by the internally reflective surfaces of the specimen holder. The optical detector produces an electrical output representative of the energy level of the light impinging thereon. This electrical output may be fed to appropriate analysis equipment to determine certain characteristics of the sample within the specimen holder.

By constructing a spectral analyzer as described herein, numerous advantages are realized. For example, by providing the spectral analyzer with an optical collector assembly that collimates the light rays from the light source into a highly concentrated beam, more light energy is focused through the specimen holder without the use of a higher intensity light source or expensive and complicated optical equipment. Additionally, by constructing the collector assembly and specimen holder so that the collimated beam enters the specimen holder at a fixed angle and then reflects repeatedly off the interior reflective walls of the specimen holder at this same fixed angle, a relatively long optical path length of a known length is created, thus improving the signal-to-noise ratio of the device without the need for expensive and complicated optical equipment. The combination of these features provides a spectral analyzer that is highly effective yet relatively compact, lightweight, and inexpensive.

BRIEF DESCRIPTION OF THE DRAWING FIGURES

A preferred embodiment of the present invention is described in detail below with reference to the attached drawing figures, wherein:

FIG. 1 is a horizontal cross sectional view of a spectral analyzer constructed in accordance with a first preferred embodiment of the present invention illustrating the optical path of its collimated beam with dashed lines and arrows;

FIG. 2 is a vertical cross sectional view of the spectral analyzer taken along line 2—2 of FIG. 1; and FIG. 3 is a horizontal cross sectional view of a spectral analyzer constructed in accordance with a second preferred embodiment of the present invention illustrating the optical path of its collimated beam with dashed lines and arrows.

DETAILED DESCRIPTION OF THE PREFERRED EMBODIMENTS

Turning now to FIGS. 1 and 2 of the drawing figures, a spectral analyzer 10 constructed in accordance with a first preferred embodiment of the invention is illustrated. The spectral analyzer broadly includes an optical collector assembly 12, a specimen holder 14, and an optical detector 16.

In more detail, the collector assembly 12 includes a substantially enclosed collector housing 18 and a light source 20 positioned therein. As illustrated in FIG. 1, the entire collector assembly of the first embodiment of the invention is preferably positioned within the confines of the specimen holder 14.

The preferred collector housing 18 includes a first internal concave surface 22 that is spherical or elliptical in shape and an opposed second internal concave surface 24 that is preferably conical in shape. The first and second concave surfaces are coated with a reflective material so that the interior walls of the collector housing are highly reflective. The second reflective surface 24 includes an exit aperture 26 formed therethrough that is covered by a clear optical window 28.

The light source 20 is positioned between the first and second concave reflective surfaces 22,24. The light source preferably produces light in the infrared spectrum and may be coupled with suitable optical filters (not shown) for narrowing the spectrum to a specific wavelength. Other suitable light sources may be used as a matter of design choice. The light source may be coupled with a modulator or chopping assembly for mechanically modulating or chopping the light beam. Similarly, the light source may be coupled with an electronic pulsing device for pulsing the light beam.

The specimen holder 14 is preferably rectangular in cross section and includes a pair of generally parallel, spaced-apart sidewalls 30,32, a pair of generally parallel, spaced-apart end walls 34,36, and a pair of generally parallel, spaced-apart top and bottom walls 38,40 that together define an elongated, hollow fluid-receiving chamber 42 therebetween. As with the collector assembly, the interior surfaces of all of the walls of the specimen holder are coated with a reflective material so that they are highly reflective.

The end wall 34 of the specimen holder 14 includes an inlet port 44 for introducing a specimen into the chamber 42, and the end wall 36 includes a corresponding outlet port 46 for discharging the specimen from the chamber. The specimen holder 14 may also be provided with a non-reflective aperture section (not shown) against which a specimen could be placed for permitting spectral analysis of the specimen.

The specimen holder 14 is preferably formed of molded synthetic resin materials such as plastic, but may be formed of other suitable materials as a matter of design choice. The specimen holder illustrated in FIGS. 1 and 2 is especially configured for the analysis of fluid specimens; however, it can also be used for the analysis of solid and gaseous samples.

The optical detector 16 detects the collimated beam produced by the collector assembly 12 after it has been reflected in the specimen holder 14. The optical detector may be positioned anywhere within or adjacent to the specimen holder 14 but is preferably positioned near the end wall 36 opposite the collector assembly 12. The optical detector 16 is preferably a photodetector that is configured for detecting the specific wavelength band of light emitted by the light source 20 and for producing an electrical output representative of the energy level of the light impinging thereon. Other conventional detector devices can also be used with the present invention. In use, the optical detector may be coupled with appropriate analysis equipment that analyzes the electrical output to determine the characteristics of the compound within the specimen holder.

In operation, a specimen to be analyzed is first introduced into the hollow chamber 42 of the specimen holder 14 through the inlet port 44. The light source 20 is then energized so that the light rays therefrom are directed toward the first and second reflective concave surfaces 22,24. The reflective surfaces reflect and collimate the light rays into a highly concentrated beam of parallel light rays as illustrated by the arrows within the collector assembly 12 in FIG. 1.

The collimated beam is directed out of the exit aperture 26 of the collector assembly 12 and into the hollow chamber 42 of the specimen holder 14. The collector assembly and specimen holder are positioned relative to one another so that the collimated beam is directed into the specimen holder at a pre-selected, fixed angle of 45° measured from the sidewalls 30,32.

After the collimated beam enters the specimen holder 14, it impinges upon the internally reflective sidewall 30 and reflects toward the opposite sidewall 32 as illustrated by the dashed lines and arrows in FIG. 1. The beam continues to reflect between the sidewalls 30,32 until it impinges upon the interior surface of the generally perpendicular end wall 36 and reflects therefrom back to the sidewall 30 and toward the opposite end wall 34. The beam continues its path toward the end wall 34 until it reflects from the generally perpendicular exterior surface 48 of the collector assembly 12. The surface 48 reverses the direction of the beam and reflects it to the sidewall 30 so that it reflects between the sidewalls, 30,32 back toward the end wall 36 until it reaches the optical detector 16.

The reflective action of the specimen holder 14 creates an optical pathway through the chamber 42 that is substantially longer than the length of the specimen holder itself. In the embodiment illustrated in FIGS. 1 and 2, the optical path length is approximately 3–4 times greater than the length of the specimen holder. Each time the light beam impinges upon one of the internally reflective surfaces of the specimen holder, it is reflected therefrom at the same fixed angle that the beam exits the reflective assembly. In the first embodiment of the invention, this angle is 45°.

When the collimated beam impinges upon the optical detector 16, the detector detects the specific wavelength band of light and produces an electrical output representative of the energy level of the light impinging thereon. As discussed above, the optical detector may be coupled with appropriate analysis equipment that analyzes the electrical output to determine the characteristics of the compound within the specimen holder 14.

FIG. 3 illustrates a spectral analyzer 100 constructed in accordance with a second preferred embodiment of the invention in which the shape of the specimen holder 102 has been changed to alter the optical path of the collimated beam. Specifically, the specimen holder 102 includes two mating segments 104,106 that are generally V-shaped in cross section and that are joined to form an enclosed chamber 108 having end walls 110,112 each having a pair of generally perpendicular segments 114,116 and 118,120. In this embodiment, the collector assembly 122 and detector assembly 124 are positioned externally of the specimen holder 102 and coupled thereto with hollow optical passageways 126,128 to allow the collimated beam created by the collector assembly to reflect off of the perpendicular segments 114–120 without interference from the collector and detector assemblies.

The collimated beam entering the specimen holder 102 is reflected off of the perpendicular segments 114–120 as illustrated by the arrows and dashed lines in FIG. 3 until it reaches the optical detector 124. The specimen holder of this embodiment creates an optical path length that is approximately 7–8 times greater than the length of specimen holder itself.

Although the invention has been described with reference to the preferred embodiment illustrated in the attached drawing figures, it is noted that equivalents may be employed and substitutions made herein without departing from the scope of the invention as recited in the claims. For example, although the drawing figures illustrate specific shapes for the specimen holder, the specimen holder may be formed in numerous shapes to yield an optical path of any desired length.

Having thus described the preferred embodiment of the invention, what is claimed as new and desired to be protected by Letters Patent includes the following:

1. A spectral analyzer comprising:

an optical collector assembly including a collector housing, and a light source positioned within the collector housing for emitting light therein, the collector housing having a plurality of spaced, internally reflective walls and an exit aperture through one of the walls, the internally reflective walls being configured to collect and collimate the light emitted from the light source into a single beam of parallel light rays that is directed out of the exit aperture;

a substantially enclosed specimen holder positioned adjacent the exit aperture of the collector for receiving the collimated beam, the specimen holder presenting a length and including a plurality of internally reflective surfaces for reflecting the collimated beam along an optical path that is substantially longer than the length of the specimen holder; and an optical detector positioned in or adjacent to the specimen holder for detecting the collimated beam after it has been reflected by the internally reflective surfaces of the specimen holder.

2. The spectral analyzer as set forth in claim 1, the collector including a first concave reflective portion and an opposed second concave reflective portion having the exit aperture formed therethrough.

3. The spectral analyzer as set forth in claim 2, wherein the first concave reflective portion is spherical in shape.

4. The spectral analyzer as set forth in claim 2, wherein the second concave reflective portion is conical in shape.

5. The spectral analyzer as set forth in claim 1, the specimen holder including an inlet port for receiving a specimen to be analyzed and an exit port for discharging the specimen.

6. The spectral analyzer as set forth in claim 1, wherein the optical collector assembly and specimen holder are positioned relative to one another so that the collimated beam enters the specimen holder and strikes one of the reflective surfaces of the specimen holder at a selected, fixed angle.

7. The spectral analyzer as set forth in claim 6, wherein the collimated beam is reflected from the internally reflective surfaces of the specimen holder at the selected, fixed angle along the entire optical path of the collimated beam.

8. The spectral analyzer as set forth in claim 6, wherein the selected fixed angle is 45°.

9. The spectral analyzer as set forth in claim 1, further including a modulator coupled with the light source for modulating the collimated beam.

10. The spectral analyzer as set forth in claim 1, wherein the specimen holder is substantially polygonal in cross section.

11. The spectral analyzer as set forth in claim 1, wherein the specimen holder is substantially rectangular in cross section.

12. The spectral analyzer as set forth in claim 1, wherein the optical path length is at least two times as long as the length of the specimen holder.

13. The spectral analyzer as set forth in claim 1, wherein the optical path length is at least three times as long as the length of the specimen holder.

* * * * *